US00PP29349P3

(12) United States Plant Patent
Wells

(10) Patent No.: US PP29,349 P3
(45) Date of Patent: May 29, 2018

(54) ***HELLEBORUS* PLANT NAMED 'MONOBYRN1'**

(50) Latin Name: *Helleborus hybrida*
Varietal Denomination: MONOBYRN1

(71) Applicant: Richard Wells, Dayton, OR (US)

(72) Inventor: Richard Wells, Dayton, OR (US)

(73) Assignee: Monrovia Nursery Co., Azusa, CA (US)

( * ) Notice: Subject to any disclaimer, the term of this patent is extended or adjusted under 35 U.S.C. 154(b) by 16 days.

(21) Appl. No.: 14/999,762

(22) Filed: Jun. 22, 2016

(65) Prior Publication Data

US 2017/0374790 P1 Dec. 28, 2017

(51) Int. Cl.
*A01H 5/02* (2018.01)

(52) U.S. Cl.
USPC ..... Plt./439
CPC ..... *A01H 5/02* (2013.01)

(58) Field of Classification Search
USPC ..... Plt./439
See application file for complete search history.

*Primary Examiner* — Susan McCormick Ewoldt
(74) *Attorney, Agent, or Firm* — Cassandra Bright

(57) ABSTRACT

A new and distinct *Helleborus* cultivar named 'MONOBYRN1' is disclosed, characterized by distinctive purple and white sepals and a large quantity of distinctive greyed-purple nectaries. The new cultivar is a *Helleborus*, suitable for ornamental garden purposes.

4 Drawing Sheets

Figure 1:
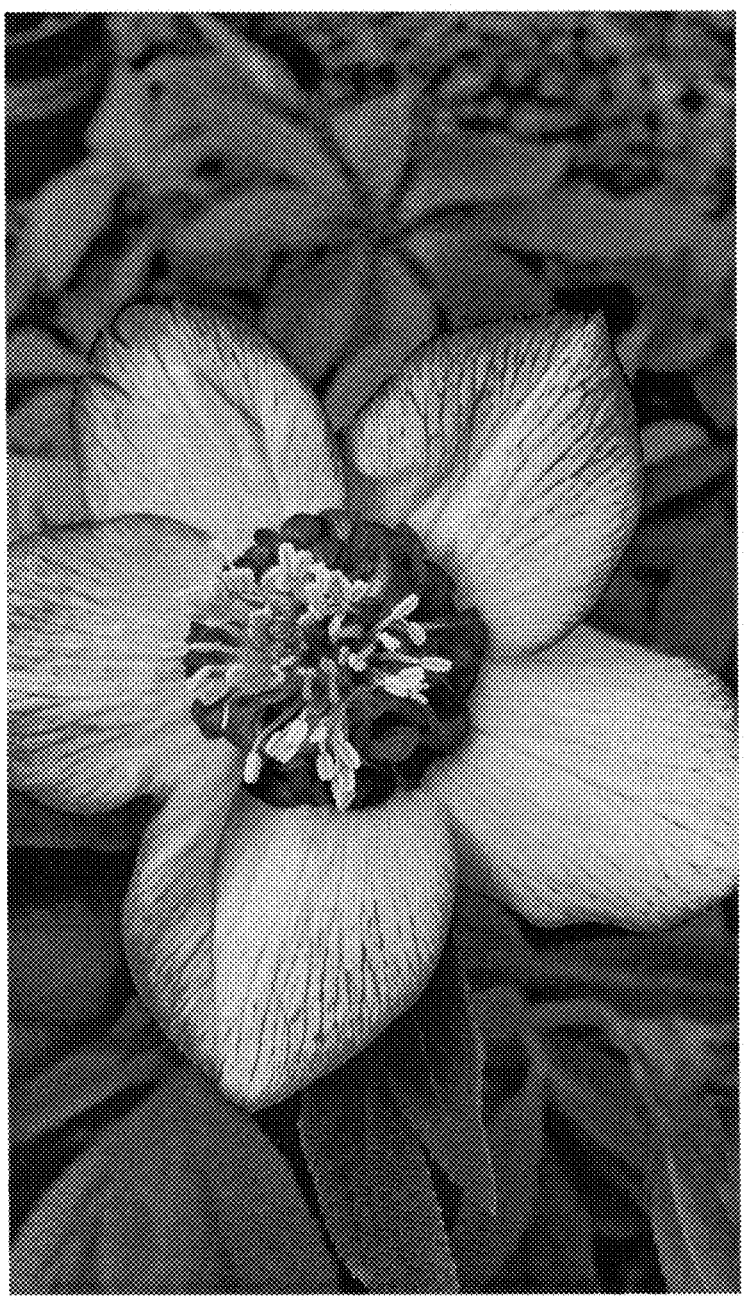

Latin name of the genus and species: *Helleborus hybrida*. Variety denomination: 'MONOBYRN1'.

BACKGROUND OF THE INVENTION

The new cultivar was selected by the inventor, Richard Wells among a planting of seedling *Helleborus hybrida*. Seed and pollen parents are unidentified *Helleborus hybrida*. This new variety was discovered February 2012 as a single plant in a field of *Helleborus hybrida* seedlings in Salem, Oreg.

After identifying the new variety as a potentially interesting selection, the inventor first organized propagation of 'MONOBYRN1' by shoot tissue culture at a commercial laboratory in Oregon, during 2012. The inventor continued controlled testing and propagation, assessing stability of the unique characteristics of this variety. Several generations have been reproduced and have shown that the unique features of this cultivar are stable and reproduced true to type.

SUMMARY OF THE INVENTION

The cultivar 'MONOBYRN1' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'MONOBYRN1' These characteristics in combination distinguish 'MONOBYRN1' as a new and distinct *Helleborus* cultivar:

1. Distinctive purple and white flowers, changing in color variation with maturity.
2. Flowers with prominent ornamental Greyed-Purple nectaries.

COMPARISON TO PARENT VARIETY

The new variety is distinguished from unidentified parent variety by the distinctive prominent nectaries colored Greyed-Purple. No other varieties in the field of unnamed, unpatented *Helleborus hybrida* plants showed such dark and prominent nectaries.

'MONOBYRN1' can be compared to the commercial variety *Helleborus* 'MONOBYRN2', co-pending, having application Ser. No. 14/999,761. Plants of the new cultivar 'MONOBYRN1' are similar to plants of 'MONOBYRN2' in most horticultural characteristics. Plants of the new cultivar 'MONOBYRN1' however, differ in the following:

1. Flowers of MONOBYRN1' have distinctive large, dark nectaries, 'MONOBYRN2' produces smaller nectaries of yellow-green flushed greyed-purple.
2. Flowers of 'MONOBYRN1' are single, and rarely double, plants of this comparator produce consistently double flowers.

COMMERCIAL COMPARISON

'MONOBYRN1' can be compared to the commercial variety *Helleborus* 'Double Ellen', unpatented. Plants of the new cultivar 'MONOBYRN1' are similar to plants of 'Double Ellen' in most horticultural characteristics. Plants of the new cultivar 'MONOBYRN1' however, differ in the following:

1. Sepal color of the new variety is lighter than that of this comparator.
2. Nectary color of the new variety is distinctively darker than the sepal coloration, producing a bi-color effect not seen in this comparator.
3. The new variety produces a single or sometimes double row of sepals surrounding a pronounced nectary. This comparator flower is produces at least 3 rows of sepals, without pronounced nectary.

'MONOBYRN1' can be compared to the commercial variety *Helleborus* 'COSEH 1090' U.S. Plant Pat. No. 26,446. Plants of the new cultivar 'MONOBYRN1' are similar to plants of 'COSEH 1090' in most horticultural characteristics. Plants of the new cultivar 'MONOBYRN1' however, differ in the following:

1. Mature sepal coloration of the new variety is Purple near Purple 77C, and 77A, mature sepal coloration of the comparator is Greyed-Purple
2. The new variety produces Greyed-Purple nectaries, the comparator produces Yellow-Green nectaries.

BRIEF DESCRIPTION OF THE PHOTOGRAPHS

The accompanying photographs illustrate the overall appearance of the new *Helleborus* 'MONOBYRN1' showing the colors as true as is reasonably possible with colored reproductions of this type. The figures depict flowers at various stages of maturity, on plants of approximately 18 months. Colors in the photographs may differ slightly from the color values cited in the detailed botanical description which accurately describes the color of 'MONOBYRN1'.

FIG. 1 shows a close-up of an aging flower. This flower is at the most mature stage before drying and losing ornamental value.

Figure 2:
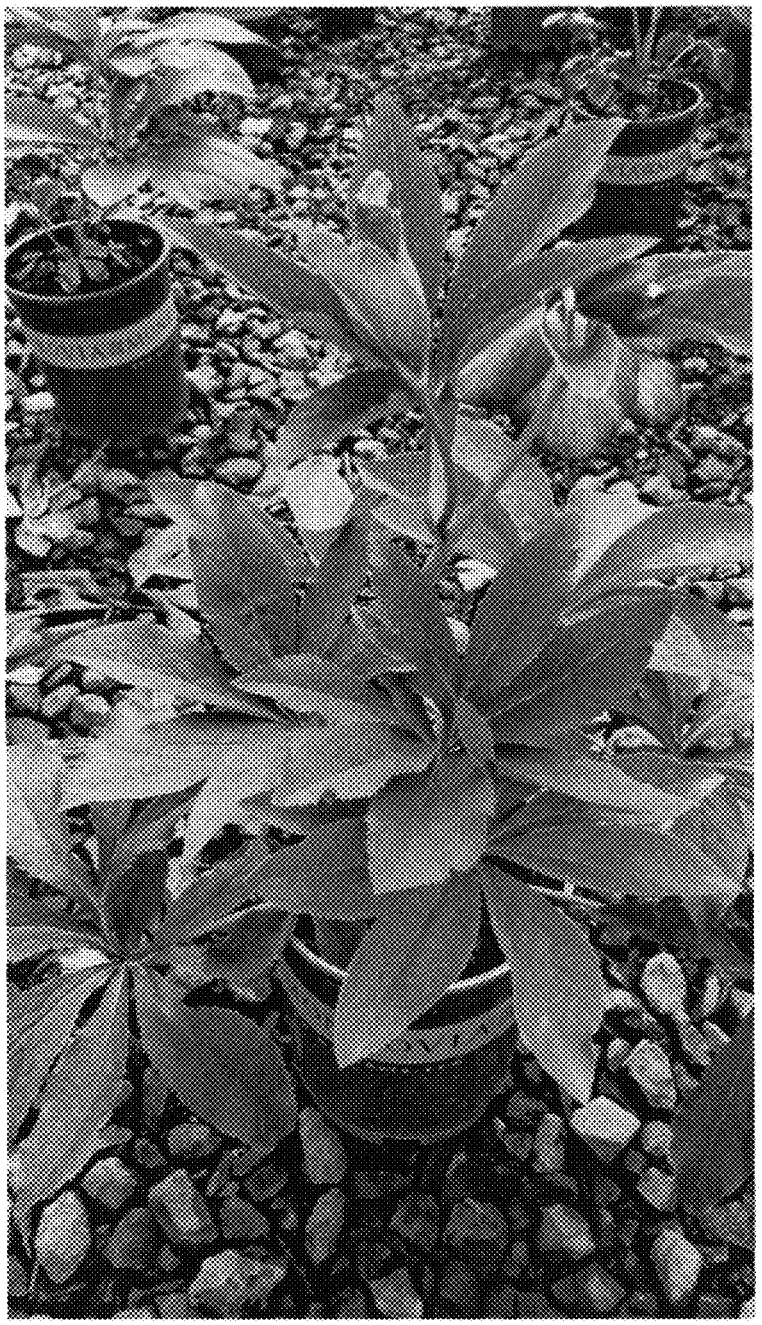
Figure 3:
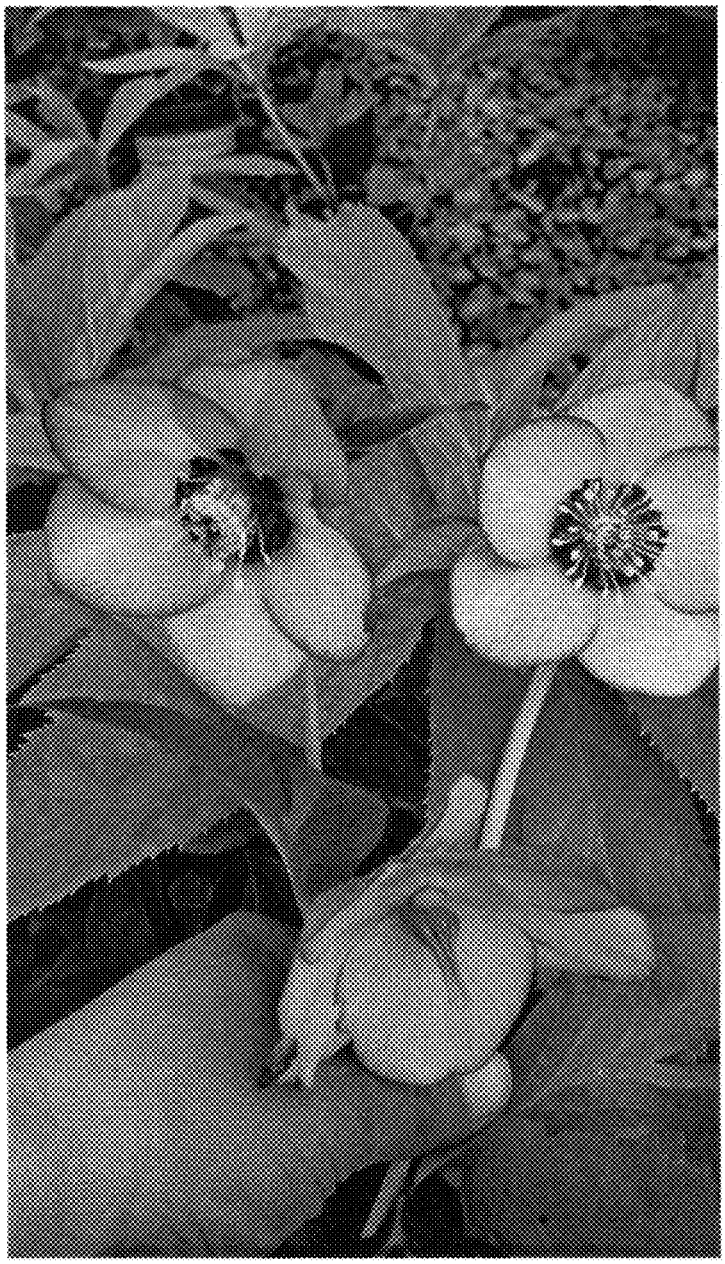

FIG. 2 depicts a mature plant, with a flower of average maturity. The flower is seen from the reverse, showing the exterior of the sepals FIG. 3 shows a close-up of 3 immature flowers. These flowers are at slight different levels of maturity, but none have fully colored purple as a mature flower.

Figure 4:
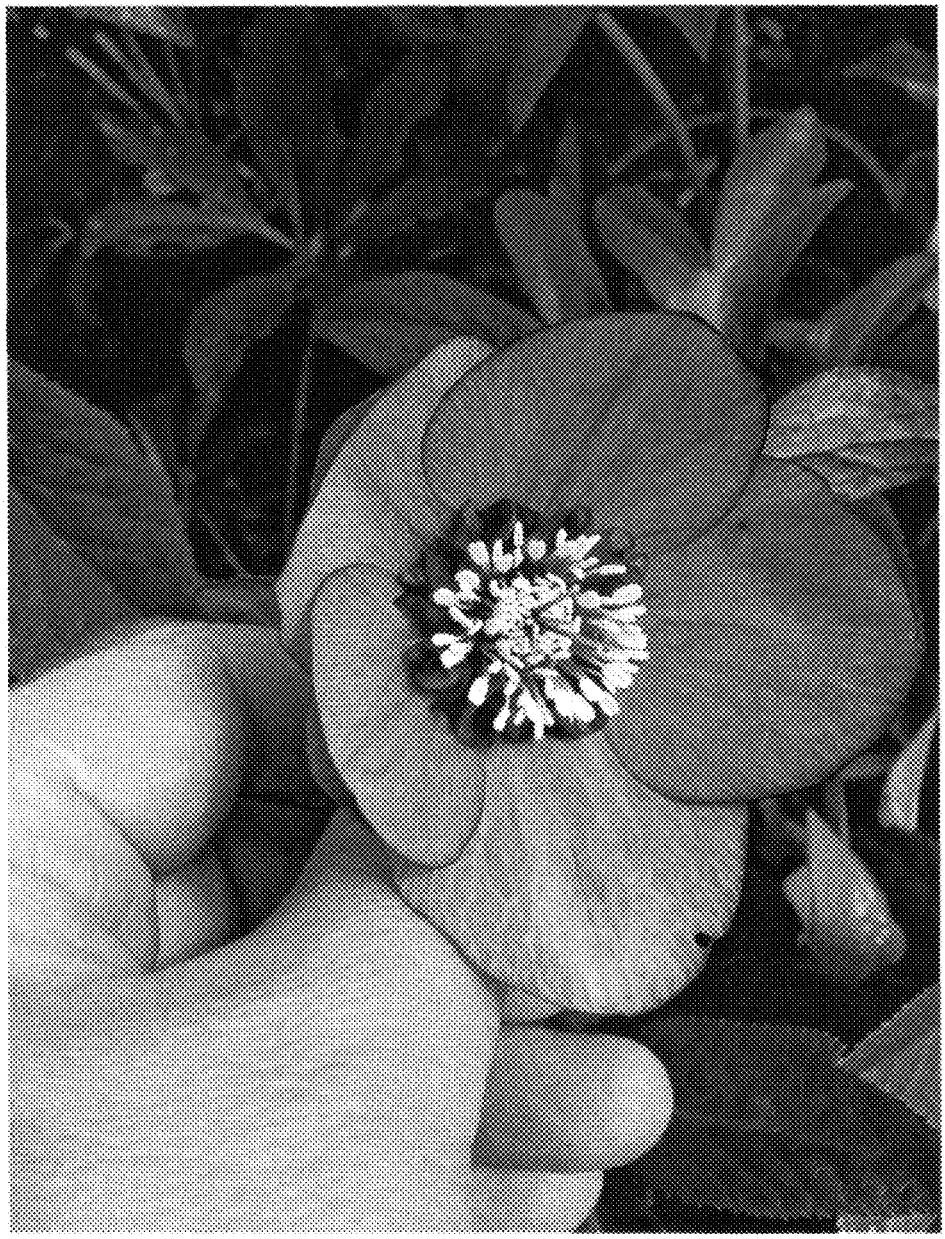

FIG. 4 shows a close-up of a mature flower.

DETAILED BOTANICAL DESCRIPTION

In the following description, color references are made to The Royal Horticultural Society Colour Chart 2007 except where general terms of ordinary dictionary significance are used. The following observations and measurements describe 'MONOBYRN1' plants grown outdoors in Salem Oreg. Plants are approximately 1 year old, in a 1 gallon nursery container. Measurements and numerical values represent averages of typical plant types.

Botanical classification: *Helleborus hybrida* 'MONOBYRN1'.

Propagation: Typically by shoot tissue culture.

*Root description.*—Single main root, moderate branching of short lateral roots. Cream to tan in color, not accurately measured with an R.H.S. chart.

Plant:

*Growth habit.*—Moderate.

*Height.*—Approximately 35 cm.

*Plant spread.*—Approximately 45 cm.

*Branching characteristics.*—No true branching. Leaves emerge direct from base of plant, or infrequently occur directly on the flowering stem.

*Age of plant described.*—Approximately 1 year.

Foliage:

*Leaf.*—Shape: Compound palmate. Quantity per stem: 1. Length: 11 to 13.0 cm. Diameter: 13.0 cm. Quantity: Approximately 20 basal leaves, per plant.

*Leaflets.*—Quantity: Average 7 to 9. Shape: Outermost leaflets elliptic. Center leaflets broadly elliptic to spatulate. Arrangement: Radial. Average Length: Average 9.0 to 11.0 cm. Average Width: Average 3.0 to 4.0 cm. Apex: Acute. Base: Attenuate. Margin: Sharply serrate. Texture of top surface: Glabrous. Texture of bottom surface: Glabrous. Appearance of top surface: Matte. Appearance of bottom surface: Matte. Aspect: Flat to very slightly reflexed downward. Color: Mature Leaflet: Upper side: Near RHS Green 137A. Under side: Near RHS Green 137D. Immature Leaflet: Upper side: Near RHS Yellow-Green 144A. Under side: Near RHS Yellow-Green 144A. Venation: Type: Palmate. Venation color upper side: Near RHS Yellow-Green 145A. Venation color under side: Center vein near RHS Yellow-Green N144B, lateral veins near Yellow-Green 147A. Petiole: Length: Average range 10 to 15 cm. Diameter: 0.7 cm. Color: Near RHS Yellow-Green 144C. Irregularly occurring blotches near RHS Greyed-Purple N186A. Lower petiole frequently near RHS Greyed-Purple N186A. Texture: Ridged, Glabrous.

Flower:

*Natural flowering season.*—Winter.

*Inflorescence type and habit.*—Singly occurring whorled radial flowers. Half dome shaped flower with upward curve. Typically flowers have a single whorl of sepals, occasionally a double whorl of sepals. Petals are modified into nectaries.

*Flower longevity on plant.*—Approximately 2 weeks.

*Quantity of flowers.*—Approximately 15 to 25, depending on environmental conditions, during peak flowering.

*Flower size.*—Diameter: Approximately 5.5 cm. Height: Average range 2.9 cm.

*Peduncle.*—Length: Approximately 2 to 12 cm. Diameter: Approximately 0.3 cm. Color: Near RHS Yellow-Green N144A, spotted near RHS Greyed-Purple 187A. Strength: Moderately strong and very flexible. Texture: Glabrous. Aspect: Slightly undulating.

*Bud.*—Shape: Oblong. Length: Approximately 2.0 cm. Diameter: Approximately 1.5 cm. Color: Near RHS Greyed-Purple N186D; base near RHS Green-White 157A and apex near RHS Greyed-Purple N186A. Rate of Opening: Approximately 3 to 7 days from color flushed bud to open flower.

*Sepals.*—Quantity: Typically 6. Length: Approximately 3.5 cm. Width: Approximately 2.4 cm. Shape: Outer sepals broad elliptic, inner sepals elliptic. Aspect: Upwardly cupped. Apex: Acute. Base: Attenuate. Margin: Entire, slightly ruffled. Color: When opening: Interior Surface: RHS Greyed-Green 193B, and White N155C. Veins near RHS Purple 77C, turning 77A towards apex. Margin 77A. Exterior Surface: RHS Yellow-White 158D and White 155C, veins near RHS Veins near RHS Purple 77A. Margin 77A. Near apex overall flush near 77B. Mature: Interior Surface: Closest to RHS Purple 77C and 77B with margin near 77A. Exterior Surface: Near RHS White 155C, veins near Purple 77B and Red-Purple 61A, colors present individually. Margin near 77A. Apical flushing near Red-Purple 71A. Aging: Interior Surface: Near RHS White 155C, veins near Red-Purple 70A. Margin near 77A. Apical flushing near Purple 77A and 77B. Exterior Surface: Near RHS White 155C, veins near Red-Purple 70A. Margin near 77A. Apical flushing near Purple 77A and 77B.

*Nectaries* (*modified petals*).—Quantity: Average 20. Shape: Tubular. Length: Approximately 0.8 cm. Diameter: Approximately 0.4 cm. Color: Near RHS Greyed-Purple 187A, basal streaks near White 155C. Texture: Glabrous.

*Fragrance.*—None detected.

Reproductive organs:

*Stamens.*—Number: Approximately 30 per flower. Filament length: Approximately 0.4 cm. Filament color: Near RHS Yellow-White 158D.

*Anthers.*—Length: 0.1 cm. Shape: Linear. Color: Near RHS Yellow-White 158B. Pollen: Amount: Scant. Color: Near RHS Yellow-White 158D.

*Pistil.*—Number: Typically 6 per flower. Length: Approximately 0.8 cm. Stigma: Shape: Club shape. Color: Near RHS Greyed-Purple N186C. Ovary: Near RHS Yellow-Green 144C.

Other characteristics:

*Disease and pest resistance.*—Not observed to be susceptible nor resistant to normal diseases and pests of *Helleborus* Typical pests include Aphid and Thrips. The most common fungal disease is *Coniotyrium hellebore*. The Genus is also known to suffer from various Nematodes, as well as *Pythium, Phytophtora* and *Rhizoctonia.*

*Temperature tolerance.*—Typically USDA Zones 3 to 9.

*Fruit/seed production.*—Not observed.

What is claimed is:

1. A new and distinct cultivar of *Helleborus* plant named 'MONOBYRN1' as herein illustrated and described.

* * * * *